US006911536B1

(12) United States Patent
Erikson et al.

(10) Patent No.: US 6,911,536 B1
(45) Date of Patent: Jun. 28, 2005

(54) TRIPLEX AND QUADRUPLEX CATALYTIC HYBRIDIZATION

(75) Inventors: Glen H. Erikson, Providenciales (TC); Jasmine I. Daksis, Richmond Hill (CA)

(73) Assignee: Ingeneus Corporation, Bridgetown (BB)

(*) Notice: Subject to any disclaimer, the term of this patent is extended or adjusted under 35 U.S.C. 154(b) by 0 days.

(21) Appl. No.: 09/713,177

(22) Filed: Nov. 15, 2000

Related U.S. Application Data

(63) Continuation-in-part of application No. 09/664,827, filed on Sep. 19, 2000, and a continuation-in-part of application No. 09/613,263, filed on Jul. 10, 2000, now Pat. No. 6,420,115, which is a continuation-in-part of application No. 09/468,679, filed on Dec. 21, 1999, now Pat. No. 6,403,313.

(51) Int. Cl.[7] .......................... C07H 21/02; C12Q 1/68
(52) U.S. Cl. ......................................... 536/23.1; 435/6
(58) Field of Search .......................... 536/23.1, 24.31, 536/22.1; 435/6

(56) References Cited

U.S. PATENT DOCUMENTS

| | | | |
|---|---|---|---|
| 4,220,450 A | 9/1980 | Maggio | |
| 4,876,187 A | 10/1989 | Duck et al. | |
| 4,963,477 A | 10/1990 | Tchen | |
| 5,011,769 A | 4/1991 | Duck et al. | |
| 5,332,659 A | 7/1994 | Kidwell | |
| 5,403,711 A * | 4/1995 | Walder et al. | 435/6 |
| 5,451,502 A * | 9/1995 | George, Jr. | 435/6 |
| 5,538,848 A | 7/1996 | Livak et al. | |
| 5,539,082 A | 7/1996 | Nielsen et al. | |
| 5,558,998 A | 9/1996 | Hammond et al. | |
| 5,660,988 A * | 8/1997 | Duck et al. | 435/6 |
| 5,705,346 A | 1/1998 | Okamoto et al. | |
| 5,707,801 A | 1/1998 | Bresser et al. | |
| 5,731,146 A * | 3/1998 | Duck et al. | 435/6 |
| 5,800,984 A | 9/1998 | Vary | |
| 5,800,992 A | 9/1998 | Fodor et al. | |
| 5,814,447 A | 9/1998 | Ishiguro et al. | |
| 5,814,516 A | 9/1998 | Vo-Dinh | |
| 5,824,477 A | 10/1998 | Stanley | |
| 5,824,557 A | 10/1998 | Burke et al. | |
| 5,846,729 A | 12/1998 | Wu et al. | |
| 5,861,124 A | 1/1999 | Hosoi et al. | |
| 5,874,555 A * | 2/1999 | Dervan et al. | 536/23.1 |
| 5,888,739 A * | 3/1999 | Pinter et al. | 435/6 |
| 5,912,332 A | 6/1999 | Agrawal et al. | |
| 5,948,897 A | 9/1999 | Sen et al. | |
| 6,013,442 A | 1/2000 | Kolesar et al. | |
| 6,017,709 A | 1/2000 | Hardin et al. | |
| 6,027,880 A | 2/2000 | Cronin et al. | |
| 6,046,004 A | 4/2000 | Wu et al. | |
| 6,048,690 A | 4/2000 | Heller et al. | |
| 6,060,242 A | 5/2000 | Nie et al. | |
| 6,107,078 A | 8/2000 | Keese et al. | |
| 6,117,657 A | 9/2000 | Usman et al. | |
| 6,251,591 B1 | 6/2001 | Wu et al. | |
| 6,255,050 B1 | 7/2001 | Nie et al. | |
| 6,255,469 B1 | 7/2001 | Seeman et al. | |
| 6,287,772 B1 | 9/2001 | Stefano et al. | |
| 6,312,925 B1 | 11/2001 | Meyer, Jr. et al. | |
| 6,420,115 B1 * | 7/2002 | Erikson et al. | 435/6 |

FOREIGN PATENT DOCUMENTS

| | | |
|---|---|---|
| GB | 2333359 A | 7/1999 |
| GB | 2338301 A | 12/1999 |
| WO | WO 97/45539 A1 | 12/1997 |
| WO | WO 00/20633 A1 | 4/2000 |
| WO | WO 00 43543 A | 7/2000 |

OTHER PUBLICATIONS

McGavin et al. A computer graphics study of multistranded DNA models. J. Mol. Graphics., vol. 7, pp. 218–232, 1989.*
Eckhart et al. Reverse transcription–polymerase chain reaction products of alternatively spliced mRNAs form DNA heteroduplexes and heteroduplex complexes. J Biol Chem., vol. 274, No. 5, pp. 2613–2615, 1999.*
Deng et al. Duplex to quadruplex equilibrium of the self-complementary oligonucleotide d (GGGGCCCC). Biopolymers, vol. 35, pp. 677–681, 1995.*
Sinden R. Formation and stability of Intramolecular triple–stranded DNA. DNA structure and function. pp. 225–227, 1994.*
Abstract to JP 5237000, Yoshitami (Sep. 17, 1993).
Abstract of Johansen and Jacobsen, *J Biomol Struct Dyn*, 16(2):205–22 (Oct. 1998).
Bohmann et al., *Science*, 238:1386–1392 (Dec. 1987).
Chan et al., *J. Mol. Med*. 75 Issue 4:267–282 (1997).
Dalrymple et al., *Nucleic Acids Research*, vol. 13, No. 21, pp. 7865–7879 (1985).
Durland et al., *Biochemistry*, 30:9246–9255 (1991).
Egholm et al., 365 *Nature* 566 (Oct. 7, 1993).
Hill et al., *Methods in Enzymology*, 278:390–416 (1997).
Kadonaga et al., *Cell*, 51:1079–1090 (Dec. 24, 1987).
U.S. Appl. No. 09/664,827, Erikson et al.
Kukreti et al. 25 *Nucleic Acids Research* 4264–4270 (1997).
Sturm et al., *Genes&Development*, 2:1582–1599 (1988).
Tomac et al., 118 *J. Am. Chem. Soc*. 5544–5552 (1996).
Watson, James, "A Personal Account of the Discovery of the Structure of DNA," (1968).
Wilson et al., *Cell*, 74:115–125 (Jul. 16, 1993).
Zhurkin et al., *J. Mol. Biol.*, vol. 239, 181–200 (1994).
U.S. Appl. No. 09/468,679, Daksis et al.
U.S. Appl. No. 09/490,273, Picard et al.

(Continued)

Primary Examiner—Jeffrey Fredman
Assistant Examiner—Suryaprabha Chunduru
(74) Attorney, Agent, or Firm—Caesar, Rivise, Bernstein, Cohen & Pokotilow, Ltd.

(57) ABSTRACT

An assay includes catalytic hybridization of targets and cleavable probes to form triplexes and quadruplexes based on Watson-Crick bonding rules. The probes contain scissile linkages that are cleaved by enzymes when hybridized to a target, yielding detectable probe fragments free of the target. The target is recycled to help catalyze the cleavage of additional intact probes to form additional detectable probe fragments, thus amplifying the signal.

62 Claims, No Drawings

OTHER PUBLICATIONS

U.S. Appl. No. 09/613,623, Erikson et al.
Sen et al., Nature 334:364–366 (1988).
Williamson et al., Cell 59:871–880 (1989).
Sen et al., Biochemistry 31:65–70 (1992).
Marsh et al., Biochemistry 33:10718–10724 (1994).
Marsh et al., Nucl. Acids Res. 23:696–700 (1995).
Mazumder et al., Biochemistry 35:13762–13771 (1996).
Baran et al., Nucleic Acids Research 25:297–303 (1997).
Floris et al., "Effect of cations on purine–purine–pyrimidine," 260 Eur. J. Biochem. 801–809 (1999).
McGavin, "Models of Specifically Paired Like (Homologous) Nucleic Acid Structures," *J. Mol. Biol.* (1971) 55, 293–298.
McGavin, "Relationships and Transformations Between Some Nucleic Acid Models," *J. Theor. Biol.* (1980) 85, 665–672.
McGavin, "Four Strand Recombination Models," *J. Theor. Biol.* (1989) 136, 135–150.
McGavin, "Four–Strand Structure, Kinks and Cruciforms in DNA," *J. Theor. Biol.* (1989) 138, 117–128.
McGavin et al., "A Computer Graphics Study of Multi-stranded DNA Models," J. Mol Graphics. (1989) 7,218–232.
Lishanski et al., "Branch migration inhibition in PCR–amplified DNA; homogeneous mutation detection", *Nucleic Acids Research*, vol. 28, No. 9, pp. e42i–e42 vii, (May 1, 2000).
Deng et al., "Duplex to quadruplex equilibrium of the self–complementary oligonucleotide" *Biopolymer*, vol. 35, No. 6, pp. 677–681, (1995).
Salisbury et al., The bi–loop, a new general four–stranded DNA motif, *Prol. Natl. Acad. Sci. USA*, vol. 94, pp. 5515–5518 (May 1997).
Eckhart, et al., *The Journal of Biological Chemistry*, vol. 274, No. 5, pp. 2613–2615, (Jan. 29, 1999).

* cited by examiner

US 6,911,536 B1

TRIPLEX AND QUADRUPLEX CATALYTIC HYBRIDIZATION

CROSS-REFERENCE TO RELATED APPLICATIONS

This application is a continuation-in-part of U.S. patent application Ser. No. 09/664,827, filed Sep. 19, 2000, and a continuation-in-part of U.S. patent application Ser. No. 09/613,263, filed Jul. 10, 2000, now U.S. Pat. No. 6,420,115 which is a continuation-in-part of U.S. patent application Ser. No. 09/468,679, filed Dec. 21, 1999, now U.S. Pat. No. 6,403,313 the disclosures of which are incorporated by reference herein in their entireties.

BACKGROUND OF THE INVENTION

1. Field of Invention

The invention relates to nucleic acid multiplexes, and more particularly to sensitive methods for accurately assaying triplex and quadruplex nucleic acid complexes employing catalytic hybridization.

2. Description of Related Art

Although nucleic acid duplexes are the most widely studied type of multiple-strand nucleic acid structures, it has been discovered that nucleic acids also form triplex and quadruplex structures under certain conditions.

Until recently, hybridization among three nucleic acid strands to form a triplex was widely believed to be confined to very limited species of nucleic acids (e.g., polypurine or polypyrimidine sequences). See, e.g., Floris et al., "Effect of cations on purine-purine-pyrimidine triple helix formation in mixed-valence salt solutions," 260 Eur. J. Biochem. 801–809 (1999). Moreover, triplex formation or hybridization was thought to be based on Hoogsteen binding between limited varieties of adjacent nucleobases, rather than Watson-Crick base pairing. See, e.g., Floris et al. and U.S. Pat. No. 5,874,555 to Dervan et al. However, the inventors have recently disclosed in several patent applications that triplex nucleic acids based on Watson-Crick base pairing can be created and used as the basis for a highly accurate and sensitive assay for specific binding. See U.S. patent applications Ser. Nos. 09/613,263 and 09/468,679, respectively filed Jul. 10, 2000 and Dec. 21, 1999.

As was the case with triplex nucleic acids, the conventional wisdom regarding quadruplex nucleic acids has been that such peculiar structures only exist under relatively extreme conditions for a relatively narrow class of nucleic acids. In particular, Sen et al. (Nature 334:364–366 (1988)) disclosed that guanine-rich oligonucleotides can spontaneously self-assemble into four-stranded helices in vitro. Sen et al. (Biochemistry 31:65–70 (1992)) disclosed that these four-stranded complexes can further associate into superstructures composed of 8, 12, or 16 oligomers.

Marsh et al. (Biochemistry 33:10718–10724 (1994), and Nucleic Acids Research 23:696–700 (1995)) disclosed that some guanine-rich oligonucleotides can also assemble in an offset, parallel alignment, forming long "G-wires". These higher-order structures are stabilized by G-quartets that consist of four guanosine residues arranged in a plane and held together through Hoogsteen base pairings. According to Sen et al. (Biochemistry 31:65–70 (1992)), at least three contiguous guanines within the oligomer are critical for the formation of these higher order structures.

It has been suggested that four-stranded DNAs play a role in a variety of biological processes, such as inhibition of HIV-1 integrase (Mazumder et al., Biochemistry 35:13762–13771 (1996)), formation of synapsis during meiosis (Sen et al., Nature 334:364–366 (1988)), and telomere maintenance (Williamson et al., Cell 59:871–880 (1989)); Baran et al., Nucleic Acids Research 25:297–303 (1997)).

It has been further suggested that controlling the production of guanine-rich quadruplexes might be the key to controlling such biological processes. For example, U.S. Pat. No. 6,017,709 to Hardin et al. suggests that telomerase activity might be controlled through drugs that inhibit the formation of guanine quartets.

U.S. Patent No. 5,888,739 to Pitner et al. discloses that G-quartet based quadruplexes can be employed in an assay for detecting nucleic acids. Upon hybridization to a complementary oligonucleotide, the G-quartet structure unfolds or linearizes, thereby increasing the distance between a donor and an acceptor on different parts of the G-quartet structure, resulting in a decrease in their interaction and a detectable change in a signal (e.g., fluorescence) emitted from the structure.

U.S. Pat. No. 5,912,332 to Agrawal et al. discloses a method for the purification of synthetic oligonucleotides, wherein the synthetic oligonucleotides hybridize specifically with a desired, full-length oligonucleotide and concomitantly form a multimer aggregate, such as quadruplex DNA. The multimer aggregate containing the oligonucleotide to be purified is then isolated using size-exclusion techniques.

Conventional assays for nucleic acids have generally been based on a duplex hybridization model, wherein a single-stranded probe specifically binds to a complementary single-stranded target sequence.

Peter Duck and his colleagues have disclosed particularly sensitive methods for detecting duplex hybridization, based on catalytic hybridization technology. See, e.g., U.S. Pat. Nos. 4,876,187, 5,011,769, 5,660,988 and 5,731,146, all to Duck et al. Briefly stated, catalytic hybridization is a method in which a large stoichiometric excess of probe is added to target in the presence of a cleaving agent adapted to specifically cleave duplexed probe. The cleaved fragments of the probe then dehybridize to provide detectable probe fragments distinguishable from intact probes, and a recycled target available for hybridization with additional intact probes. Thus, the target acts as a sort of catalyst for the cleaving step; hence the name "catalytic hybridization" (a term apparently coined by Walder et al. in U.S. Pat. No. 5,403,711).

As a single target can catalyze the cleavage of a virtually unlimited number of intact probes to provide a multitude of detectable probe fragments, the signal is amplified relative to more conventional detection methods in which each target accounts for only a single signal once hybridized with a probe.

Despite the foregoing developments, the full potential of catalytic hybridization has neither been fully appreciated nor fully exploited.

All references cited herein are incorporated herein by reference in their entireties.

BRIEF SUMMARY OF THE INVENTION

Accordingly, the invention provides a catalytic hybridization composition comprising:
 a probe containing at least one probe nucleobase sequence and at least one scissile linkage sequence;
 an enzyme adapted to cleave said at least one scissile linkage sequence;

a nucleic acid target containing at least one target nucleobase sequence associated with said nucleobase sequence of said probe by Watson-Crick bonding to form a multiplex structure; and a hybridization medium containing said probe, said enzyme and said nucleic acid target, wherein at least one of said probe nucleobase sequence and said target nucleobase sequence is double-stranded.

Also provided is a method for assaying binding, said method comprising:

providing a probe containing at least one probe nucleobase sequence and at least one scissile linkage sequence;

providing an enzyme adapted to cleave said at least one scissile linkage sequence;

providing a target containing at least one target nucleobase sequence;

combining said probe, said enzyme and said target in a hybridization medium further containing water, a buffer and at least one promoter;

incubating said hybridization medium to hybridize said probe nucleobase sequence to said target nucleobase sequence by Watson-Crick bonding to form a multiplex, wherein at least one of said probe nucleobase sequence and said target nucleobase sequence is double-stranded;

cleaving hybridized probes at said at least one scissile linkage to provide unbound probe fragments; and detecting said unbound probe fragments to assay binding between said probe and said target.

DETAILED DESCRIPTION OF THE INVENTION

In the assay of the invention, the target is reacted with a complementary probe having a scissile linkage to form a multiplex comprising the target and probe hybridized to each other. Preferably, the probe is designed such that, upon cleavage by an enzyme which is capable of specifically cleaving the probe-target multiplex at the scissile linkage, probe fragments are released which are detectable.

The scissile linkage of the probe is capable of being cleaved or disrupted without cleaving or disrupting the balance of the probe or the target. As used within the context of the present invention, a scissile linkage is any connecting chemical structure which joins two nucleic acid or nucleic acid analogue sequences, which is capable of being selectively cleaved without cleavage of the nucleic acid sequences to which it is joined. The scissile linkage may be a single bond or a multiple unit sequence. An example of such a chemical structure is a RNA molecule. Other chemical structures which may be suitable as a scissile linkage are DNA molecules, an amino acid sequence, an abasic nucleotide molecule or any carbohydrate polymer (e.g., cellulose or starch). When the scissile linkage is a nucleic acid molecule, it should differ from the nucleic acid sequence of the flanking sequences.

Preferred probe molecules of the present invention generally have the structure $[(NA_1)_x(S)_z(NA_2)_y]_n$, where $NA_1$ and $NA_2$ are nucleobase-containing sequences composed of nucleic acids or nucleic acid analogues, S is a scissile linkage, x, y, and z are integers from 1–100 and n is an integer from 1–10. Within certain particularly preferred embodiments of the invention, $NA_1$ and $NA_2$ can independently range from 3 to 40 nucleotides, and when S is a nucleic acid, can range in size from 2 to 20 nucleotides. In addition, it should be understood that as utilized within the context of the present invention, each of x, y and z can vary with each iteration of n.

The scissile linkage is preferably about 2 to about 12 nucleotides in length (i.e., z=about 2 to about 12).

Within certain embodiments, $NA_1$, and $NA_2$ as described above are DNA molecules which may or may not have the same sequence. Alternatively, $NA_1$ and $NA_2$ may be constructed of RNA, which may or may not have the same sequence, or a combination of RNA and DNA. The DNA or RNA can be derived from naturally occurring sources, or they can be synthetically formed. Each of $NA_1$ and $NA_2$ can be from about 5 bases to 10,000 bases in length.

Within certain other embodiments, $NA_1$ or $NA_2$ may be composed of nucleic acid analogues such as methyl phosphonates, carbamates, amidates, triesters, and/or peptide nucleic acids (PNAs), with PNAs being most preferred among the nucleic acid analogues. It is also possible to construct the entire backbone of the probe (including the scissile linkage) from RNA.

When n is greater than one in the formula $[(NA_1)_x(S)_z(NA_2)_y]_n$, the probe comprises more than one ($NA_1$-S-$NA_2$) unit. In such embodiments, the ($NA_1$-S-$NA_2$) units in the probe can be the same or different from each other randomly, or in a defined pattern.

In particularly preferred embodiments of the invention, probes have the structure $[(NA_1)_x(S)_z(NA_2)_y]_n$, where $NA_1$, and $NA_2$ are nucleic acid sequences, S is a scissile nucleic acid linkage, and n is an integer from 1 to 10. Within such embodiments, $NA_1$ and $NA_2$ are different nucleic acid sequences that are not complementary to each other, and S is a scissile linkage which is capable of being cleaved or disrupted without cleaving or disrupting $NA_1$, or $NA_2$, or a target nucleic acid sequence capable of hybridizing to the $NA_1$, or $NA_2$ sequences, wherein if the scissile linkage is a nucleic acid sequence it is RNA when both $NA_1$ and $NA_2$ are DNA sequences, or the scissile linkage is DNA when both $NA_1$ and $NA_2$ are RNA sequences.

Probes of the present invention may also have one or more detectable markers attached to one or both ends (e.g., $NA_1$ or $NA_2$). The marker may be virtually any molecule or reagent which is capable of being detected, representative examples of which include radioisotopes or radiolabeled molecules, fluorescent molecules, fluorescent antibodies, enzymes, or chemiluminescent catalysts.

In certain embodiments, a portion of the probe on one side of the scissile linkage contains a marker whose signal is attenuated by a quenching agent contained in a portion of the probe on the opposite side of the scissile linkage. In such embodiments, the cleaving of the probe places the marker outside the influence of the quenching agent, thereby yielding a non-attenuated signal.

In certain other embodiments, a portion of the probe on one side of the scissile linkage contains a marker whose signal is amplified by an amplification agent contained in a portion of the probe on the opposite side of the scissile linkage. In such embodiments, the cleaving of the probe places the marker outside the influence of the amplification agent, thereby yielding an attenuated signal.

The probe can contain at least one interspersed sequence that is not cleavable by the enzyme. The interspersed sequence can comprise DNA or DNA analogues, or nucleotide residues selected from the group consisting of phosphonates, phosphotriesters, phosphoroamidates and 2'-0 alkyl and aryl ribonucleotide.

Enzymes suitable for use in the invention are defined by their functional characteristics. Thus, certain suitable enzymes will cleave only RNA sequences of nucleotides in a multiplex structure, or will cleave only nucleobases having predetermined backbone characteristics. RNAaseH is a preferred enzyme, particularly when obtained from *E. coli.* Further examples of suitable enzymes include the enzymatic cleaving agents of U.S. Pat. Nos. 6,117,657 to Usman et al. and U.S. Pat. No. 6,107,078 to Keese et al.

In embodiments, non-specific cleavage of the probe may be suppressed with at least one single-stranded ribonuclease inhibitor selected from the group consisting of vanadate, RNAsin, and Inhibit—ACE.

The probes of the present invention may also be linked to a solid support either directly, or through a chemical linker. Representative examples of solid supports include silicaceous, cellulosic, polymer-based, or plastic materials. In certain embodiments, the support may be electrically conductive, for example, when the support and the test sample form a part of an electric circuit.

Methods for constructing such nucleic acid probes (and adjacent or flanking sequence oligonucleotides, as described below), may be readily accomplished by one of ordinary skill in the art, given the disclosure provided herein. Particularly preferred methods are described for example by: Matteucci and Caruthers, J. Am. Chem. Soc. 103:3185, 1981; Beaucage and Caruthers, Tetrahedron Lett. 22:1859–1862, 1981; U.S. Pat. Nos. 4,876,187 and 5,011,769; Ogilvie et al., Proc. Natl. Acad. Sci. USA 85:8783–8798, 1987; Usman et al., J. Am. Chem. Soc. 109:7845–7854, 1987; Wu et al., Tetrahedron Lett. 29:4249–4252, 1988; Chaix et al., Nuc. Acids Res. 17:7381–7393, 1989; Wu et al., Nuc. Acids Res. 17:3501–3517, 1989; McBride and Caruthers, Tetrahedron Lett. 24:245–248, 1983; Sinha et al., Tetrahedron Lett. 24:5843–5846, 1983; Sinha et al., Nuc. Acids Res. 12:4539–4557, 1984; and Gasparutto et al., Nuc. Acids Res. 20:5159–5166, 1992.

Unlike certain triplexes and quadruplexes discussed in the Background Section above, the preferred multiplex structures of the invention contain at least three strands of nucleic acid bonded together according to traditional Watson-Crick bonding rules. As used herein, the term "Watson-Crick bonding" is intended to define specific association between opposing pairs of nucleic acid (and/or nucleic acid analogue) strands via matched, opposing bases. While the formation of a Watson-Crick multiplex may sometimes be referred to as a hybridization event herein, that is merely for convenience and is not intended to limit the scope of the invention with respect to how the formation of a Watson-Crick multiplex can be best characterized.

The multiplex structures of the invention are preferably triplexes or quadruplexes. Each strand of the multiplex independently comprises a nucleic acid (e.g., DNA, RNA, MRNA, hnRNA, rRNA, tRNA or CDNA) or a nucleic acid analogue. Suitable nucleic acids include, e.g., DNA or RNA. Preferred nucleic acid analogues contain an uncharged or partially charged backbone (i.e., a backbone having a charge that is not as negative as a native DNA backbone).

At least a portion of the multiplex structure is isolated, purified, artificial or synthetic.

In certain quadruplex embodiments, a strand of the probe and a strand of the target are anti-parallel to each other. These embodiments are defined as having mirror complementarity. In these embodiments, a major groove of the probe is placed in a major groove of the target.

In other quadruplex embodiments, a strand of the probe and a strand of the target are parallel to each other. In these embodiments, which possess "nested complementarity," a major groove of the probe is placed in a minor groove of the target.

In certain triplex and quadruplex embodiments, each nucleobase binds to no more than two other nucleobases. Thus, in addition to the traditional Watson-Crick base pairs, such embodiments include the following Watson-Crick base triplets: A-T-A, T-A-T, U-A-T, T-A-U, A-U-A, U-A-U, G-C-G and/or C-G-C (including $C^+$-G-C, and/or any other ionized species of base).

In certain quadruplex embodiments wherein the probe is defined as a first and a second strand and the target is defined as a third and a fourth strand, it is believed that the first and third strands also bind to each other, in addition to: (a) the binding between opposing bases of the first and second strands; (b) the binding between opposing bases of the third and fourth strands; and (c) the binding between opposing bases of the second and fourth strands.

In certain embodiments of the multiplex structure of the invention, no strand is contiguous with another strand. That is, there are at least three separate strands. Although folded conformations and the like (e.g., hairpin turns, etc.) are within the scope of the invention, folded portions of a single strand do not make the strand count more than once toward the minimum of three separate strands.

Multiplex structures of the invention preferably do not rely on Hoogsteen bonding or G-G quartets for maintenance of the multiplex structure, although insignificant amounts of Hoogsteen bonding and/or G-G quartets may be present. That is, multiplex structures of the invention are preferably substantially free of Hoogsteen bonding, and substantially free of G-G quartets.

In embodiments, the target is a PCR amplified product.

The multiplexes of the invention can be present in solution, on a solid support, in vitro or in vivo. The solid support can be electrically conductive (e.g., an electrode) or non-conductive.

Multiplex structures of the invention can be provided by a method comprising: (a) providing a probe containing at least one probe nucleobase sequence and at least one scissile linkage sequence; (b) providing an enzyme adapted to cleave said at least one scissile linkage sequence; (c) providing a target containing at least one target nucleobase sequence; (d) combining said probe, said enzyme and said target in a hybridization medium further containing water, a buffer and at least one promoter; and (e) incubating said hybridization medium to hybridize said probe nucleobase sequence to said target nucleobase sequence by Watson-Crick bonding to form a multiplex, wherein at least one of said probe nucleobase sequence and said target nucleobase sequence is double-stranded.

The hybridization medium can include any conventional medium known to be suitable for preserving nucleotides. See, e.g., Sambrook et al., "Molecular Cloning: A Lab Manual," Vol. 2 (1989). For example, the medium can comprise nucleotides, water, buffers and standard salt concentrations. When divalent cations are used exclusively to promote multiplex formation, chelators such as EDTA or EGTA should not be included in the reaction mixtures.

Specific binding between complementary bases occurs under a wide variety of conditions having variations in temperature, salt concentration, electrostatic strength, and buffer composition. Examples of these conditions and methods for applying them are known in the art.

Unlike many Hoogsteen-type multiplexes, which are unstable or non-existent at pH levels above about 7.6, the Watson-Crick multiplexes of the invention are stable over a wide range of pH levels, preferably from about pH 5 to about pH 9.

Moreover, the inventive multiplexes do not require the presence of homopyrimidine sequences or homopurine sequences, as in certain prior art multiplexes. For example, the target sequence can contain 25% to 75% purine bases and 75% to 25% pyrimidine bases in any order.

It is preferred that multiplexes be formed at a temperature of about 2° C. to about 55° C. for about two hours or less. The incubation time is preferably less than five minutes, even at room temperature. Longer reaction times are not required, but incubation for up to 24 hours in most cases did not adversely affect the multiplexes. The fast binding times of Watson-Crick multiplexes of the invention contrast with the much longer binding times for Hoogsteen multiplexes.

The promoter in the hybridization medium is preferably an intercalating agent or a cation. The intercalating agent can be, e.g., a fluorophore, such as a member selected from the group consisting of YOYO-1, TOTO-1, ethidium bromide, ethidium homodimer-1, ethidium homodimer-2 and acridine.

Suitable cations include, e.g., monovalent cations, such as $Na^+$(preferably at a concentration of 40 mM to 200 mM), $K^+$(preferably at a concentration of 40 mM to 200 mM), and other alkali metal ions; divalent cations, such as alkaline earth metal ions (e.g., $Mg^{+2}$ and $Ca^{+2}$) and divalent transition metal ions (e.g., $Mn^{+2}$, $Ni^{+2}$, $Cd^{+2}$, $Co^{+2}$ and $Zn^{+2}$); and cations having a positive charge of at least three, such as $Co(NH_3)_6^{+3}$, trivalent spermidine and tetravalent spermine. $Mn^{+2}$ is preferably provided at a concentration of 10 mM to 30 mM. $Mg^{+2}$ is preferably provided at a concentration of 15 mM to 20 mM. $Ni^{+2}$ is preferably provided at a concentration of about 20 mM. In embodiments, $Mg^{+2}$ and $Mn^{+2}$ are provided in combination at a concentration of 10 mM each, 15 mM each, 20 mM each, 25 mM each or 30 mM each (i.e., 10–30 mM each).

The amount of cation added to the medium in which the multiplex forms depends on a number of factors, including the nature of the cation, the concentration of probe, the concentration of target, the presence of additional cations and the base content of the probe and target. The preferred cation concentrations and mixtures can routinely be discovered experimentally.

Although not required, other promoters include, e.g., single stranded binding proteins such as Rec A protein, T4 gene 32 protein, E. coli single stranded binding protein, major or minor nucleic acid groove binding proteins, viologen and additional intercalating substances such as actinomycin D, psoralen, and angelicin. Such facilitating reagents may prove useful in extreme operating conditions, for example, under abnormal pH levels or extremely high temperatures.

The invention provides a rapid, sensitive, environmentally friendly, and safe method for assaying binding. The inventive assay can be used to, e.g., identify accessible regions in folded nucleotide sequences, to determine the number of mismatched base pairs in a hybridization complex, and to map genomes.

The invention not only detects the presence of specific probe-target binding, but also provides qualitative and quantitative information regarding the nature of interaction between a probe and target. Thus, the invention enables the practitioner to distinguish among a perfect match, a one base pair mismatch, a two base pair mismatch, a three base pair mismatch, a one base pair deletion, a two base pair deletion and a three base pair deletion arising between a sequence in the double-stranded probe or single-stranded probe and in a sequence in the double-stranded or single-stranded target.

Embodiments of the invention comprise calibrating the measured signal (e.g., optical, fluorescence, chemiluminescence, electrochemiluminescence, electrical or electromechanical properties) for a first probe-target mixture against the same type of signal exhibited by other probes combined with the same target, wherein each of the other probes differs from the first probe by at least one base.

A calibration curve can be generated, wherein the magnitude of the measured signal (e.g., fluorescent intensity) is a function of the binding affinity between the target and probe. As the binding affinity between the target and a plurality of different probes varies with the number of mismatched bases, the nature of the mismatch(es) (A-G vs. A-C vs. T-G vs. T-C, etc.), the location of the mismatch(es) within the multiplex, etc., the assay of the invention can be used to sequence the target.

In embodiments, the signal measured can be the fluorescent intensity of a fluorophore included in the test sample. In such embodiments, the binding affinity between the probe and target can be directly or inversely correlated with the intensity, depending on whether the fluorophore signals hybridization through signal quenching or signal amplification. Under selected conditions, the fluorescent intensity generated by intercalating agents can be directly correlated with probe-target binding affinity, whereas the intensity of preferred embodiments employing a non-intercalating fluorophore covalently bound to the probe can be inversely correlated with probe-target binding affinity. The fluorescent intensity decreases for non-intercalating fluorophores as the extent of matching between the probe and target increases, preferably over a range inclusive of 0–2 mismatches and/or deletions, more preferably over a range inclusive of 0–3 mismatches and/or deletions.

The invention enables quantifying the binding affinity between probe and target. Such information can be valuable for a variety of uses, including designing antisense drugs with optimized binding characteristics.

The assay of the invention is preferably homogeneous. The assay can be conducted without separating the cleaved probe fragments from hybridization complex, free intact probe and free target prior to detecting the magnitude of the measured signal. The assay does not require a gel separation step, thereby allowing a great increase in testing throughput. Quantitative analyses are simple and accurate. Consequently the binding assay saves a lot of time and expense, and can be easily automated. Furthermore, it enables binding variables such as buffer, pH, ionic concentration, temperature, incubation time, relative concentrations of probe and target sequences, intercalator concentration, length of target sequences, length of probe sequences, and possible cofactor (i.e., promoter) requirements to be rapidly determined.

The assay can be conducted in, e.g., a solution within a well or microchannel, on an impermeable surface or on a biochip. In certain embodiments, the target is provided in the hybridization medium before the probe, and the probe is provided in dehydrated form prior to rehydration by contact with the hybridization medium.

In certain embodiments, the inventive assay is conducted without providing a signal quenching agent on the target or on the probe.

The invention obviates the need to denature the target prior to assaying. It is surprising that the inventors have been able to specifically assay triplexes and quadruplexes, wherein the interaction between the probes and targets is based on Watson-Crick base pairing (at least in the sense that A binds to T (or U, in the case of RNA) and G binds to C), rather than the very limited Hoogsteen model of multiplex hybridization of, e.g., Pitner et al., supra.

Probes of the invention are preferably 2 to 75 bases long (more preferably 5 to 30 bases long) and targets are 8 to 3.3 ×10$^9$ base pairs long. At least one of the probe and the target must be double-stranded. For example, the probe can be single or double-stranded and the target can be, e.g., double-stranded genomic DNA, which can contain a haplotype. Thus, suitable probes for use in the inventive assay include, e.g., dsDNA, dsRNA, DNA:RNA hybrids, dsPNA, PNA:DNA hybrids and other single and double-stranded nucleic acids and nucleic acid analogues having uncharged or partially-charged backbones. The length of the probe can be selected to match the length of the target.

The instant invention does not require the use of radioactive probes, which are hazardous, tedious and time-consuming to use, and need to be constantly regenerated. Probes of the invention are preferably safe to use and stable for years. Accordingly, probes can be made or ordered in large quantities and stored.

In embodiments, the probe is labeled with a multi-molecule signaling complex or a redox pair, or with a label that elicits chemiluminescent or electrochemiluminescent properties.

When a fluorescent intercalator is not present in the hybridization medium, it is preferred that the probe or target (preferably the probe) have a fluorescent label covalently bound thereto. The label is preferably a non-intercalating fluorophore or an intercalating fluorophore. In such embodiments, the fluorophore is preferably bound to the probe at either end. Preferred fluorescent markers include biotin, rhodamine, acridine and fluorescein, and other markers that fluoresce when irradiated with exciting energy.

The excitation wavelength is selected (by routine experimentation and/or conventional knowledge) to correspond to this excitation maximum for the fluorophore being used, and is preferably 200 to 1000 nm. Fluorophores are preferably selected to have an emission wavelength of 200 to 1000 nm. In preferred embodiments, an argon ion laser is used to irradiate the fluorophore with light having a wavelength in a range of 400 to 540 nm, and fluorescent emission is detected in a range of 500 to 750 nm.

The assay of the invention can be performed over a wide variety of temperatures, such as, e.g., from about 2 to about 60° C. Certain prior art assays require elevated temperatures, adding cost and delay to the assay. On the other hand, the invention can be conducted at room temperature or below (e.g., at a temperature below 25° C.).

The reliability of the invention is independent of guanine and cytosine content in said target. Since G-C base pairs form three hydrogen bonds, while A-T base pairs form only two hydrogen bonds, target and probe sequences with a higher G or C content are more stable, possessing higher melting temperatures. Consequently, base pair mismatches that increase the GC content of the hybridized probe and target region above that present in perfectly matched hybrids may offset the binding weakness associated with a mismatched probe.

The inventive assay is extremely sensitive, thereby obviating the need to conduct PCR amplification of the target. For example, it is possible to assay a test sample having a volume of about 20 microliters, which contains about 10 femtomoles of target and about 10 femtomoles of probe. Embodiments of the invention are sensitive enough to assay targets at a concentration of $5\times10^{-9}$ M, preferably at a concentration of not more than $5\times10^{-10}$ M. Embodiments of the invention are sensitive enough to employ probes at a concentration of $5\times10^{-9}$ M, preferably at a concentration of not more than $5\times10^{-10}$ M. It should go without saying that the foregoing values are not intended to suggest that the method cannot detect higher concentrations.

The ratio of probe (e.g., first and second strands) to target (e.g., third and fourth strands) is preferably about 100:1 to about 1000:1.

In certain embodiments of the inventive assay, conditions of hybridization are subject to transitory or periodic changes. For example, a force (e.g., electric, magnetic or mechanical) may be applied to the sample prior to or concurrent with measuring the signal as taught in U.S. Application Serial No. 09/490,273, filed Jan. 24, 2000.

While the invention has been described in detail and with reference to specific examples thereof, it will be apparent to one skilled in the art that various changes and modifications can be made therein without departing from the spirit and scope thereof.

What is claimed is:

1. A catalytic hybridization composition comprising:
   a probe containing at least one probe nucleobase sequence and at least one scissile linkage sequence;
   an enzyme adapted to cleave said at least one scissile linkage sequence;
   a nucleic acid target containing at least one target nucleobase sequence associated with said nucleobase sequence of said probe by Watson-Crick bonding to form a multiplex structure; and
   a hybridization medium containing said probe, said enzyme and said nucleic acid target,
   wherein at least one of said probe nucleobase sequence and said target nucleobase sequence is double-stranded.

2. The composition of claim 1, wherein at least a portion of said multiplex structure is isolated, purified, artificial or synthetic triplex.

3. The composition of claim 1, wherein said probe is single stranded and said target is double stranded.

4. The composition of claim 1, wherein at least a portion of said probe is double stranded.

5. The composition of claim 4, wherein at least a portion of one strand of said probe comprises RNA, mRNA, hnRNA, tRNA or cDNA.

6. The composition of claim 1, wherein at least a portion of said multiplex structure is an isolated, purified, artificial or synthetic quadruplex.

7. The composition of claim 6, wherein a major groove of said probe is placed in a major groove of said target.

8. The composition of claim 6, wherein a major groove of said probe is placed in a minor groove of said target.

9. The composition of claim 1, wherein at least a portion of said probe comprises a nucleic acid or a nucleic acid analogue.

10. The composition of claim 1, wherein at least a portion of said probe comprises a nucleic acid analogue containing an uncharged or partially charged backbone.

11. The composition of claim 1, wherein each nucleobase binds to no more than two other nucleobases.

12. The composition of claim 1, wherein said composition is substantially free of self-hybridized strands.

13. The composition of claim 1, wherein said multiplex structure is substantially free of Hoogsteen binding.

14. The composition of claim 1, wherein said multiplex structure is substantially free of G-G quartets.

15. The composition of claim 1, wherein said probe is 5 to 75 nucleobases.

16. The composition of claim 1, wherein said target is genomic DNA.

17. The composition of claim 1, wherein said target includes a haplotype in genomic DNA.

18. The composition of claim 1, wherein said target comprises PCR amplified products.

19. The composition of claim 1, wherein said multiplex structure is free of solid support.

20. The composition of claim 1, wherein said multiplex structure is bound to a solid support.

21. The composition of claim 20, wherein said solid support is not electrically conductive.

22. The composition of claim 20, wherein said solid support is electrically conductive.

23. The composition of claim 1, wherein said at least one probe nucleobase sequence is from 2 to 30 bases long and said target is at least 8 base pairs long.

24. A method for assaying binding, said method comprising:
providing a probe containing at least one probe nucleobase sequence and at least one scissile linkage sequence;
providing an enzyme adapted to cleave said at least one scissile linkage sequence;
providing a target containing at least one target nucleobase sequence;
combining said probe, said enzyme and said target in a hybridization medium further containing water, a buffer and at least one promoter;
incubating said hybridization medium to hybridize said probe nucleobase sequence to said target nucleobase sequence by Watson-Crick bonding to form a multiplex, wherein at least one of said probe nucleobase sequence and said target nucleobase sequence is double-stranded;
cleaving hybridized probes at said at least one scissile linkage to provide unbound probe fragments; and
detecting said unbound probe fragments to assay binding between said probe and said target.

25. The method of claim 24, wherein an incubation temperature is from 2° C. to 60° C.

26. The method of claim 24, wherein said hybridization medium is buffered to a pH of about 5 to about 9.

27. The method of claim 24, wherein said at least one promoter is an intercalating agent.

28. The method of claim 27, wherein said at least one promoter is an intercalating fluorophore, and a fluorescent intensity of a test medium containing said multiplex structure is directly correlated with a binding affinity of said probe for said target.

29. The method of claim 28, wherein said intercalating fluorophore is a member selected from the group consisting of YOYO-1, TOTO-1, ethidium bromide, ethidium homodimer-1, ethidium homodimer-2 and acridine.

30. The method of claim 24, wherein said at least one promoter is tethered to said probe.

31. The method of claim 24, wherein said at least one promoter is a monovalent cation.

32. The method of claim 24, wherein said at least one promoter is a cation having a valency greater than one.

33. The method of claim 32, wherein said at least one promoter is at least one member selected from the group consisting of alkali metal cations, alkaline earth metal cations, transition metal cations, $Co(NH_3)_6^{+3}$, trivalent spermidine and tetravalent spermidine.

34. The method of claim 32, wherein said cation is $K^+$ or $Na^+$ provided at a concentration of 40 mM to 200 mM.

35. The method of claim 24, wherein said target is provided in said hybridization medium before said probe, and wherein said probe is provided in dehydrated form prior to rehydration by contact with said hybridization medium.

36. The method of claim 24, wherein said incubation time is not more than about 24 hours.

37. The method of claim 24, wherein probe-target hybridization is detected as a change in a fluorescent, chemiluminescent, electrochemiluminescent or electrical signal.

38. The method of claim 37, wherein an intensity of said signal is correlated with a binding affinity between said probe and said target.

39. The method of claim 38, wherein said probe is covalently labeled with a non-intercalating fluorophore and said intensity is inversely correlated with said binding affinity.

40. The method of claim 39, wherein said non-intercalating fluorophore is a member selected from the group consisting of biotin, rhodamine and fluorescein.

41. The method of claim 37, wherein said method is a homogeneous assay.

42. The method of claim 24, wherein said probe is covalently labeled with a marking agent on a first side of said at least one scissile linkage and a quenching agent on a second side of said at least one scissile linkage, wherein said quenching agent quenches a signal of said marking agent when said probe is intact and does not quench said signal after said probe is cleaved.

43. The method of claim 24, wherein said probe is covalently labeled with a marking agent on a first side of said at least one scissile linkage and a amplification agent on a second side of said at least one scissile linkage, wherein said amplification agent amplifies a signal of said marking agent when said probe is intact and does not amplify said signal after said probe is cleaved.

44. The method of claim 24, further comprising separating intact probes from said probe fragments.

45. The method of claim 24, wherein a ratio of said probe to said target is from 100:1 to 1000:1.

46. The method of claim 24, wherein concentrations of said probe and said target are not more than $5 \times 10^{-10}$ M.

47. The method of claim 24, wherein said at least one promoter is a minor groove nucleic acid binding molecule, which binds in a non-intercalating manner and binds with an association constant of at least $10^3 M^{-1}$.

48. The method of claim 24, wherein conditions of hybridization are subject to transitory or periodic changes.

49. The method of claim 48, wherein the changes are caused by applying a force.

50. The method of claim 49, wherein the force applied is electric, magnetic or mechanical.

51. The method of claim 24, wherein cleaved probe and unhybridized probe remain in solution.

52. The method of claim 24, wherein said enzyme will cleave only RNA sequences of nucleotides in a multiplex structure.

53. The method of claim 24, wherein said enzyme will cleave only nucleobases having predetermined backbone characteristics.

54. The method of claim 24, wherein a backbone structure of said probe is composed entirely of RNA.

55. The method of claim 54, wherein said at least one scissile linkage sequence is about 2 to about 12 nucleotides in length.

56. The method of claim 24, wherein said probe contains at least one interspersed sequence that is not cleavable by said enzyme.

57. The method of claim 56, wherein said at least one interspersed sequence comprises DNA or DNA analogues.

58. The method of claim 57, wherein said at least one interspersed sequence comprises nucleotide residues selected from the group consisting of phosphonates, phosphotriesters, phosphoroamidates and 2'-0 alkyl and aryl ribonucleotide.

59. The method of claim 24, further comprising suppressing non-specific cleavage of the probe with at least one single-stranded ribonuclease inhibitor selected from the group consisting of vanadate, RNAsin, and Inhibit—ACE.

60. The method of claim 24, wherein said enzyme is RNAaseH.

61. The method of claim 60, wherein said RNAaseH enzyme is obtained from *E. coli*.

62. The composition of claim 1, wherein said probe comprises an electrically, electromechanically or optically active reporter group adapted to emit a detectable signal.

* * * * *